United States Patent
Itoh et al.

(10) Patent No.: US 10,511,790 B2
(45) Date of Patent: Dec. 17, 2019

(54) IMAGE CAPTURE DEVICE AND BIOMETRIC AUTHENTICATION DEVICE

(71) Applicant: SHARP KABUSHIKI KAISHA, Sakai, Osaka (JP)

(72) Inventors: Shin Itoh, Sakai (JP); Tohru Murata, Sakai (JP); Kazuhiro Tsuchida, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 0 days.

(21) Appl. No.: 16/066,635

(22) PCT Filed: Sep. 29, 2016

(86) PCT No.: PCT/JP2016/078792
§ 371 (c)(1),
(2) Date: Jun. 27, 2018

(87) PCT Pub. No.: WO2017/115512
PCT Pub. Date: Jul. 6, 2017

(65) Prior Publication Data
US 2019/0014271 A1    Jan. 10, 2019

(30) Foreign Application Priority Data
Dec. 28, 2015 (JP) .................. 2015-257044

(51) Int. Cl.
*H04N 5/33* (2006.01)
*A61B 5/1171* (2016.01)
(Continued)

(52) U.S. Cl.
CPC ............... *H04N 5/33* (2013.01); *A61B 5/117* (2013.01); *A61B 5/1171* (2016.02); *G02B 5/30* (2013.01);
(Continued)

(58) Field of Classification Search
None
See application file for complete search history.

(56) References Cited

U.S. PATENT DOCUMENTS

| 2007/0037318 A1* | 2/2007 | Kim .................. B23K 26/0643 438/106 |
| 2007/0058841 A1 | 3/2007 | Miura et al. |

(Continued)

FOREIGN PATENT DOCUMENTS

| JP | 2004-173826 A | 6/2004 |
| JP | 2007-075305 A | 3/2007 |

(Continued)

OTHER PUBLICATIONS

Akihiro Hara et al., "A study of a contactless finger vein authentication system using moving images", The 31th Symposium on Cryptography and Information Security Kagoshima, Japan, Jan. 21-24, 2014, pp. 1 to 4.

*Primary Examiner* — Eileen M Adams
(74) *Attorney, Agent, or Firm* — ScienBiziP, P.C.

(57) ABSTRACT

Image capturing accuracy is improved while a simple optical system is used. An image capture device includes: a polarizing filter that blocks non-transmitted light that has been in polarized light of an infrared ray radiated from a light source and has not been transmitted through an image capturing target and transmitted light that has been in the polarized light and has been transmitted through the image capturing target without diffusion inside the image capturing target, and transmits transmitted light that has been in the polarized light and has been diffused inside the image capturing target and transmitted therethrough; and an image sensor that receives the light that has been transmitted through the polarizing filter and captures an image of the image capturing target.

2 Claims, 8 Drawing Sheets

(51) Int. Cl.
*G02B 5/30* (2006.01)
*G06K 9/00* (2006.01)
*H04N 5/335* (2011.01)
*A61B 5/117* (2016.01)

(52) U.S. Cl.
CPC ......... G06K 9/00033 (2013.01); H04N 5/335 (2013.01); *G06K 2009/0006* (2013.01)

(56) References Cited

U.S. PATENT DOCUMENTS

| | | | |
|---|---|---|---|
| 2011/0288385 A1* | 11/2011 | Stamatas | A61B 5/0059 600/306 |
| 2014/0180129 A1* | 6/2014 | Kostenich | A61B 1/041 600/476 |
| 2014/0337930 A1* | 11/2014 | Hoyos | H04L 63/10 726/4 |

FOREIGN PATENT DOCUMENTS

| | | |
|---|---|---|
| JP | 2011-100317 A | 5/2011 |
| JP | 2014-132992 A | 7/2014 |
| WO | 2008/013181 A1 | 1/2008 |
| WO | 2011/145392 A1 | 11/2011 |

\* cited by examiner

| 12: SEMICONDUCTOR LASER CHIP |
| 13: LIGHT-EMITTING POINT |
| 21a, 21b: ELECTRODE |
| 22: LIGHT-EMITTING LAYER |
| 23: RIDGE STRIPE |

IMAGE CAPTURE DEVICE AND BIOMETRIC AUTHENTICATION DEVICE

TECHNICAL FIELD

The present invention relates to an image capture device that captures an image of a site including biological information and a biometric authentication device that includes the image capture device.

BACKGROUND ART

In a case of photographing a living body, such as a vein, which is positioned under a skin, there is a method in which light is radiated from a palm side of a hand or a pad side of a finger and transmitted light that is transmitted to a backside of the hand or a backside of the finger is used. For example, PTL 1 discloses a method of obtaining a vein pattern of a finger by, in a state where a grip such as a doorknob is grasped, radiating light from a pad side of the finger and detecting transmitted light, which is transmitted through the finger, by an image capture unit arranged on a backside of the finger.

CITATION LIST

Patent Literature

PTL 1: Japanese Unexamined Patent Application Publication No. 2007-75305 (published on Mar. 29, 2007)

SUMMARY OF INVENTION

Technical Problem

However, by the method disclosed in PTL 1, an image is captured in the state where a grip or the like is grasped, so that the method is not suitable for authentication using a vein of an entire finger but suitable for authentication using, for example, a vein on the backside of the finger between a first joint and a second joint of the finger (refer to a paragraph [0017]).

Moreover, in order to clearly photograph a vein pattern in a region from a first joint to a second joint of one finger, it is necessary to arrange a plurality of light sources in a longitudinal direction of the finger, and, furthermore, a size of a hole in which the light sources are arranged is required to be smaller than a width of the finger (refer to a paragraph [0029] and FIG. 7). When the size of the hole in which the light sources are arranged is larger than the width of the finger, light is leaked, so that there is a possibility that saturation is caused around a contour of the finger due to the leaked light or the leaked light is reflected by a surface of the finger and thus contrast of an image is reduced (refer to the paragraph [0029]).

As above, with the method disclosed by PTL 1, a site a clear image of which is able to be obtained is limited. Moreover, in order to obtain a clear image, it is required to arrange the plurality of light sources with close attention.

In addition, light is radiated to a finger to thereby perform vein authentication in the finger, but a difference is generated between amounts of light transmitted through the finger depending on a site of the finger, to which the light is radiated. Though an amount of transmitted light is large at a knuckle of a finger which is a joint part of the finger, an amount of transmitted light is small at a pad of the finger, which is positioned between a knuckle and a knuckle of the finger, since a thickness of the finger and an amount of fat thereof are increased compared with those of the knuckle of the finger. Thus, in an obtained image, an image of a knuckle part of the finger is distinct and a vein thereof is clear, but an image of a pat part of the finger is indistinct and a vein thereof is unclear.

When an amount of light to be radiated is increased in order to increase the amount of the transmitted light at the pad part of the finger, an obtained image becomes an unclear image in which halation (phenomenon that a periphery of an object is blurred in white) is caused at the knuckle part of the finger and image capturing accuracy is deteriorated.

In addition, light that is leaked from a space between fingers at a time of radiating light to a finger and directly reaches an image sensor is also a factor that causes halation.

The invention is made in view of the aforementioned problems, and an object thereof is to provide an image capture device and a biometric authentication device that are capable of improving image capturing accuracy while using a simple optical system.

Solution to Problem

In order to solve the aforementioned problems, an image capture device according to an aspect of the invention is an image capture device that captures, as an image capturing target, an image of a site including biological information, including: a light source that radiates polarized light of an infrared ray; a polarizing filter that blocks non-transmitted light that has been in the polarized light radiated from the light source and has not been transmitted through the image capturing target and transmitted light that has been in the polarized light and has been transmitted through the image capturing target without diffusion inside the image capturing target, and transmits transmitted light that has been in the polarized light and has been diffused inside the image capturing target and transmitted therethrough; and an image sensor that receives the light that has been transmitted through the polarizing filter and captures an image of the image capturing target.

Advantageous Effects of Invention

According to the aspect of the invention, it is possible to improve image capturing accuracy while using a simple optical system.

DESCRIPTION OF EMBODIMENTS

[Embodiment 1]
(Configuration of Image Capture Device)

An image capture device according to the invention is an image capture device that captures an image of a living body of a user for biometric authentication. Specifically, an image of a living body of a user is captured by using transmitted light of light which has been radiated to the living body and transmitted through the living body. The living body as an image capturing target is a site including biological information, and examples thereof include a finger. When an image of the site including biological information is captured by the image capture device, it is possible to acquire the biological information of a vein pattern of a finger.

Figure 1:
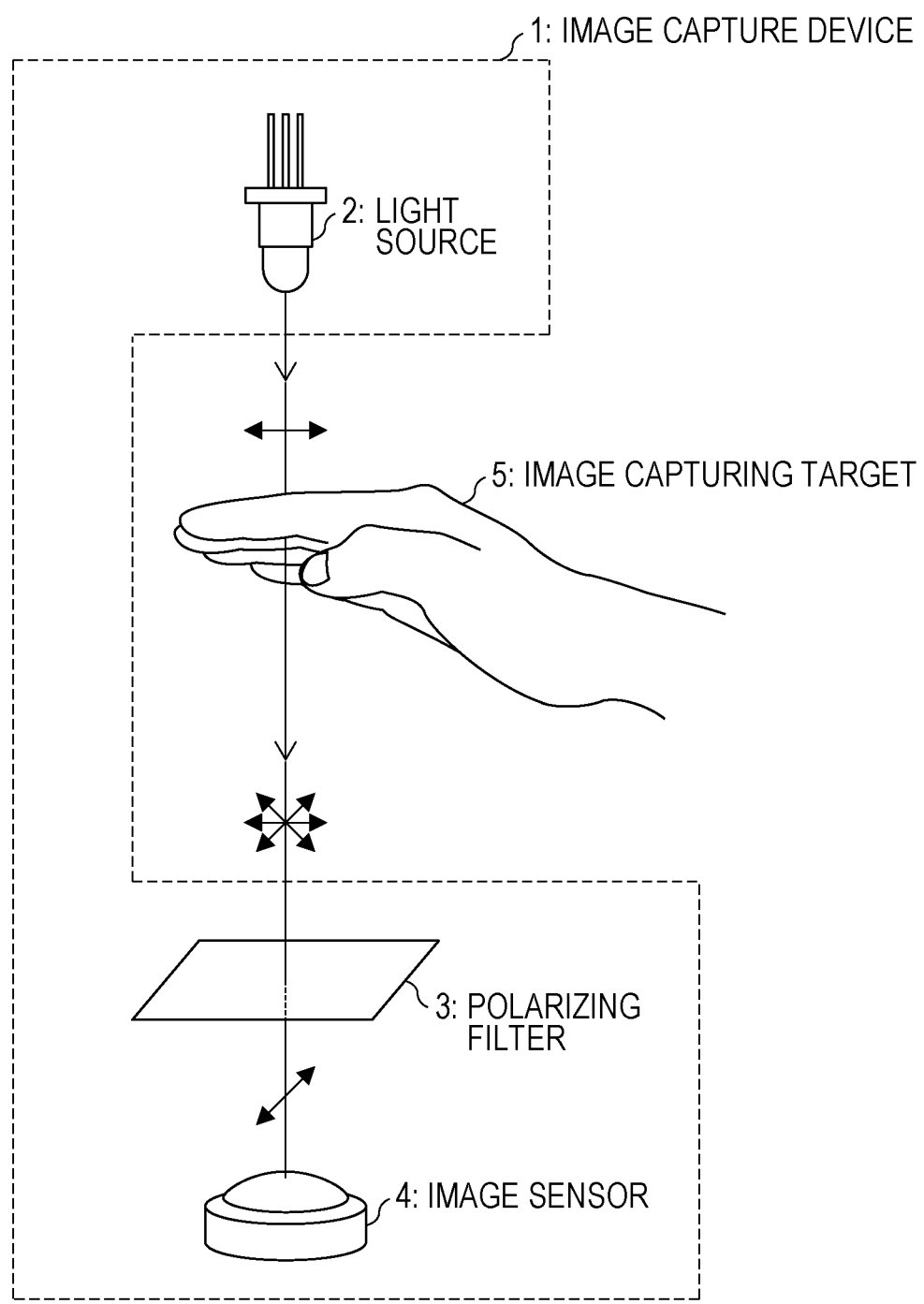
FIG. 1 is a schematic view illustrating an image capture device according to an embodiment of the invention.

Hereinafter, a case where a vein pattern of a finger of a user is acquired by capturing an image of the finger will be cited as an example to thereby describe the image capture device according to an embodiment of the invention with reference to FIG. 1. FIG. 1 is a schematic view illustrating an image capture device 1 according to the present embodiment.

The image capture device 1 includes a light source 2, a polarizing filter 3, and an image sensor 4 as illustrated in FIG. 1. Note that, for ease of understanding component members of the image capture device 1, FIG. 1 illustrates only a schematic configuration.

The light source 2 is a light source which radiates polarized light of an infrared ray and radiates light toward an image capturing target 5 so that biological information has sufficient contrast on an image captured by the image sensor 4. The light source 2 may be a semiconductor laser that radiates polarized light of an infrared ray. Alternatively, one in which a wavelength filter for radiating light having a specific wavelength and a polarizing filter for radiating light having a specific polarization plane are provided in a light source, which radiates non-polarized light, so as to radiate polarized light of an infrared ray may be used as the light source 2. Description will be given below by assuming a case where the light source 2 is a semiconductor laser that radiates polarized light of an infrared ray.

In the semiconductor laser, light radiated from an active layer of a semiconductor laser chip repeatedly reciprocates between two cleaved end surfaces of the semiconductor laser chip and then is emitted from one of the end surfaces, so that emitted light from the semiconductor laser is light having a specific polarization plane. A semiconductor laser of a ridge stripe type is a representative semiconductor laser that is suitable for taking out light having a specific polarization plane.

Here, in a case where a semiconductor laser is used as the light source 2, a filter such as the above-described wavelength filter or polarizing filter is not required to be used for the light source 2. Accordingly, it is possible to suppress loss of light, that is, reduction in intensity of light of the light source due to transmission through a filter, thus making it possible to improve image capturing accuracy of the image capture device 1. In addition, the filter is not required, so that the light source 2 is able to be made compact and also able to be mounted on mobile equipment. Furthermore, since the filter is not required to be provided, it is possible to suppress cost of the light source 2 so as to be low.

Note that, in FIG. 1, the light source 2 is arranged so that radiated light of the light source 2 is vertically incident on the image capturing target 5. This is because, in a case where light is made vertically incident on the image capturing target 5, it is possible to effectively suppress reflection of the light. However, the invention is not limited thereto. For example, the light source 2 may be arranged so that radiated light of the light source 2 is obliquely incident on the image capturing target 5.

Though details will be described later, a part of light (in this case, light radiated from a backside of a finger) which is radiated from the light source 2 toward the image capturing target 5 enters the image capturing target 5, and, while repeatedly being diffused, a part of the light is absorbed by a vein in this process and is then finally emitted from a surface (in this case, a pad side of the finger) on a side opposite to a light incident surface of the image capturing target 5. Another part of the light radiated from the light source 2 toward the image capturing target 5 is reflected by a surface of the image capturing target 5. Furthermore, still another part of the light radiated from the light source 2 toward the image capturing target 5 is not blocked by the image capturing target 5 and passes through a space (in this case, a space between fingers) or a periphery of the image capturing target 5 without reflection or diffusion.

The image sensor 4 is arranged on a surface side (in this case, the pad side of the finger) which is on the side opposite to the light incident surface of the image capturing target 5, and the polarizing filter 3 is arranged between the image sensor 4 and the image capturing target 5. The polarizing filter 3 is a filter that blocks non-transmitted light which has been in the light radiated from the light source 2 toward the image capturing target 5 and has not been transmitted through the image capturing target 5, that is, has not been blocked by the image capturing target 5 and has passed through a space or a periphery of the image capturing target 5, and transmitted light which has been in the radiated light and has been transmitted through the image capturing target 5 without diffusion inside the image capturing target 5, and transmits transmitted light which has been in the radiated light and has been repeatedly diffused inside the image capturing target 5 and transmitted through the image capturing target 5. Specifically, the polarizing filter 3 is arranged so that a light-transmitting surface thereof is orthogonal to a main polarization plane of the light source 2. Though details will be described later, thereby, the polarizing filter 3 blocks the non-transmitted light which has been in the radiated light from the light source 2 and has not been transmitted through the image capturing target 5 and the transmitted light which has been in the radiated light and has been transmitted through the image capturing target 5 without diffusion inside the image capturing target 5, and transmits a part of the transmitted light which has been in the radiated light and has been diffused inside the image capturing target 5 and transmitted therethrough.

The image sensor 4 receives the light that has been transmitted through the polarizing filter 3 and thereby captures an image of the image capturing target 5. Specifically, the image sensor 4 receives the light that has been transmitted through the polarizing filter 3, that is, the transmitted light that has been diffused inside the imaging target 5 and transmitted therethrough, and thereby generates a captured image that has brightness distribution according to biological information.

(Method of Capturing Image of Living Body)

In the image capture device 1 according to the present embodiment, as an image capturing method of the image capturing target 5, a method by which an image of a living body of a user is captured by using transmitted light which has been in light radiated toward the living body and has been diffused inside the living body and transmitted therethrough is adopted. Hereinafter, a case where a vein pattern of a finger of a hand of a user is acquired by capturing an image of the finger will be cited as an example to thereby describe the image capturing method by the image capture device 1 with reference to FIG. 2.

Figure 2:
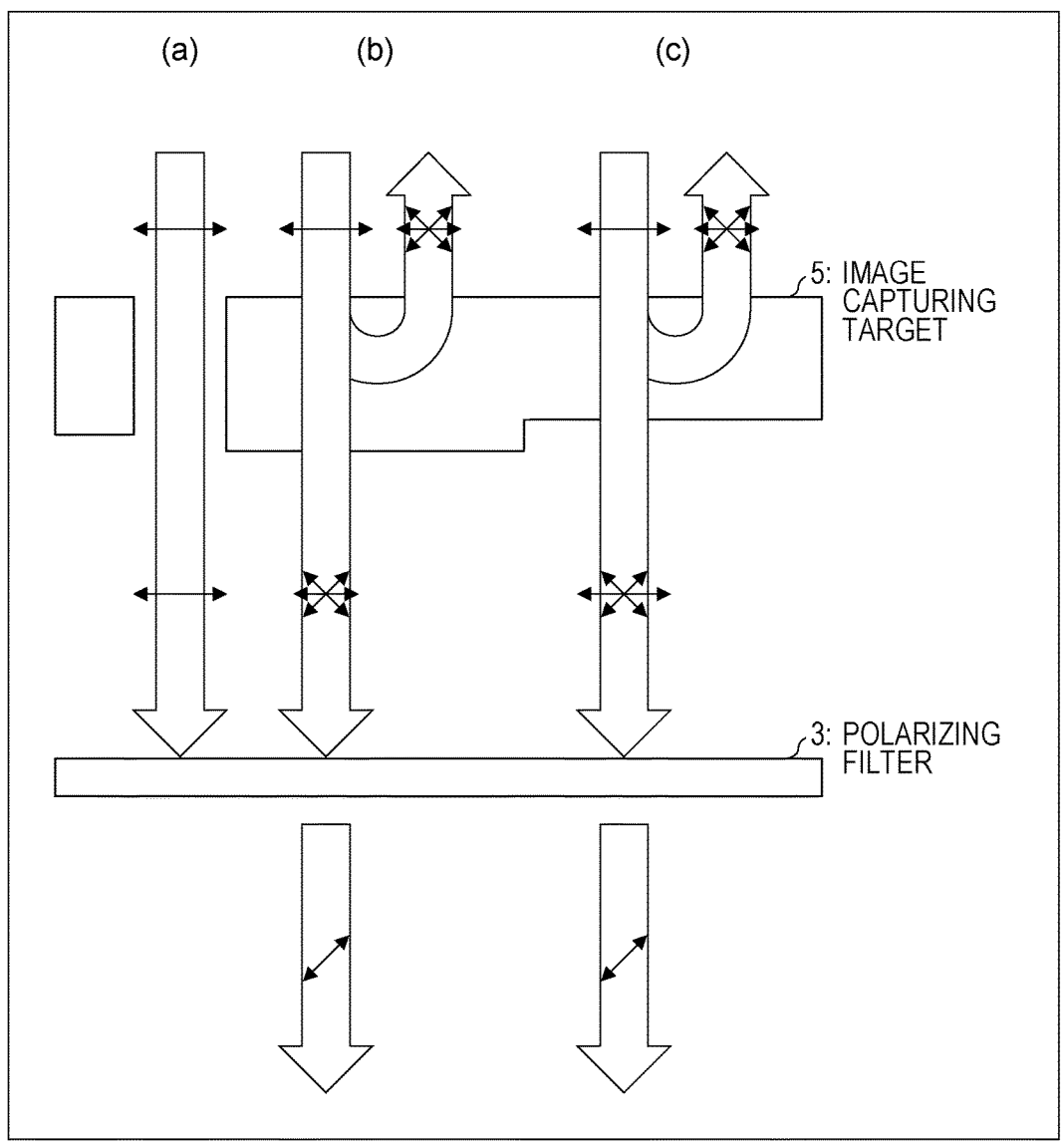
FIG. 2 is a view illustrating polarized states of light radiated from a light source according to the embodiment of the invention, in which (a) illustrates a polarized state when the light passes through a space of an image capturing target, (b) illustrates a polarized state when the light is transmitted through a part at which a thickness of the image capturing target is thick, and (c) illustrates a polarized state when the light is transmitted through a part at which the thickness of the image capturing target is thin.

FIG. 2 is a view illustrating polarized states of light radiated from the light source 2, in which (a) illustrates a polarized state when the light passes through a space of the image capturing target 5, and each of (b) and (c) illustrates a change of a polarized state of the light when the light is diffused inside the image capturing target 5 and transmitted through or reflected from the image capturing target 5. In this case, (b) and (c) illustrate the changes of the polarized states when the light is diffused inside the image capturing target 5 and transmitted through or reflected from the image capturing target 5 at parts of the image capturing target 5, which have different thicknesses. For example, FIG. 2(b) illustrates a part of a pad (between a knuckle and a knuckle) of a finger, which is a part whose thickness is thick, and FIG. 2(c) illustrates a knuckle part of the finger, which is a part whose thickness is thin.

Note that, in FIG. 2, for illustration which is easy to understand and schematic, (a) illustrates the space of the image capturing target 5 as a hole, and (c) illustrates the thickness of the image capturing target 5 so as to be thin compared with (b). Moreover, each of arrows in the figure schematically indicates a polarization direction of the light.

A part of radiated light radiated from the light source 2 toward the image capturing target 5 passes through the space of the image capturing target 5 without being transmitted through the image capturing target 5 as illustrated in FIG. 2(a). A polarization plane of the non-transmitted light that has passed through the space of the image capturing target 5 is maintained. Note that, the similar is applied to non-transmitted light that passes through a periphery of the image capturing target 5 without being transmitted through the image capturing target 5, and a polarization plane of the non-transmitted light that has passed through the periphery of the image capturing target is also maintained.

On the other hand, a different part of the radiated light from the light source 2 is diffused inside the image capturing target 5 and then transmitted through or reflected from the image capturing target 5 as illustrated in FIG. 2(b). Specifically, the different part of the radiated light from the light source 2 enters the image capturing target 5 and, while repeatedly being diffused, is emitted from a pad side of the finger. In this process, a part of the light is absorbed by a vein. The light diffused inside the image capturing target 5 is diffused in various directions and is therefore emitted in a state where no specific polarization plane is included. Note that, reflection light that is diffused inside the image capturing target 5 and then returns to a side of the light source 2 is emitted in the state where no specific polarization plane is included.

As illustrated in FIG. 2(c), although light that enters a part of the image capturing target 5, the thickness of which is thin, is also diffused inside the image capturing target 5 and then transmitted through or reflected from the image capturing target 5, since the thickness of the image capturing target 5 is thin in FIG. 2(c), the light is less likely to be diffused, so that the most part of the transmitted light is emitted in a state of maintaining the polarization plane without diffusion. Note that, the reflection light that is diffused inside the image capturing target 5 and then returns to the side of the light source 2 is emitted in the state where no specific polarization plane is included.

The non-transmitted light that has passed through the space or the periphery of the image capturing target 5, the transmitted light that has been transmitted through the image capturing target 5 while maintaining the polarization plane, and the transmitted light that has been diffused inside the image capturing target 5 and transmitted through the image capturing target 5 without including a specific polarization plane reach up to the polarizing filter 3. Since the polarizing filter 3 is arranged so that the light-transmitting surface thereof is orthogonal to the main polarization plane of the radiated light from the light source 2, neither the non-transmitted light that has passed through the space or the periphery of the image capturing target 5 nor the transmitted light that has been transmitted through the image capturing target 5 while maintaining the polarization plane is transmitted through the polarizing filter 3. On the other hand, only light of the transmitted light that has been diffused inside the image capturing target 5 and transmitted therethrough and has the same polarization plane as the light-transmitting surface of the polarizing filter 3 is transmitted through the polarizing filter 3.

In this manner, a part of the transmitted light that has been diffused inside the image capturing target 5 and transmitted therethrough is transmitted through the polarizing filter 3 and received by the image sensor 4. Intensity of light that has been diffused in a vein part inside the image capturing target 5 and then transmitted through the polarizing filter 3 is lower than intensity of light that has been diffused in a part other than the vein and then transmitted through the polarizing filter 3, so that an captured image in which brightness distribution according to the vein, that is, biological information is reproduced is generated by the image sensor 4. This is because infrared light is easy to be absorbed by a vein.

When the non-transmitted light that has passed through the space or the periphery of the image capturing target 5 enters the image sensor 4 without passing through the polarizing filter 3, since light intensity of the non-transmitted light is higher than that of the transmitted light that has been diffused inside the image capturing target 5 and transmitted therethrough, saturation is cased in a part of a captured image, which the non-transmitted light reaches. Moreover, since the non-transmitted light causes halation, a ridge line of the image capturing target 5 becomes unclear. Then, in the image capture device 1 according to the present embodiment, the non-transmitted light that has passed through the space or the periphery of the image capturing target 5 is blocked by the polarizing filter 3, so that it is possible to obtain a captured image in which brightness distribution of diffused transmitted light according to biological information is excellently reproduced.

Moreover, as illustrated in FIGS. 2(b) and (c), thicknesses of a living body differ between sites, and thicknesses from a skin surface to a vein also differ. For example, the thickness is thick at the pad part of the finger illustrated in FIG. 2(b), so that light that enters the pad part of the finger is easily diffused and an amount of light to be transmitted is reduced. On the other hand, the thickness is thin at the knuckle part of the finger illustrated in FIG. 2(c), so that light that enters the knuckle part of the finger is less likely to be diffused and a large amount of the light is easily transmitted.

As above, a transmission amount of light in the pad part of the finger is small compared with a transmission amount of light in the knuckle part of the finger, so that the pad part of the finger is displayed in a captured image so as to be dark compared with the knuckle part of the finger, and thus there is a possibility that brightness unevenness is caused in the captured image and necessary biological information is not reproduced in the captured image.

In such a case where brightness unevenness is caused, when an image is captured in short exposure time so as to match a part of FIG. 2(c), which is to be brightly displayed, an image of a part of FIG. 2(b), which is to be darkly displayed, becomes black-out and unclear. On the other hand, when an image is captured in long exposure time so as to match the part of FIG. 2(b), which is to be darkly displayed, halation, overexposure, and the like are caused in an image of the part of FIG. 2(c), which is to be brightly displayed, so that biological information is not able to be collected sufficiently.

Then, when focusing on a difference of polarization ratios of transmitted light between a site of FIG. 2(b) and a site of FIG. 2(c), while transmitted light that is transmitted through the site of FIG. 2(b) does not have a specific polarization plane, in transmitted light that is transmitted through the site of FIG. 2(c), intensity of light having the same polarization plane as a main polarization plane of radiated light is high.

Accordingly, when the polarizing filter 3 is arranged so that the light-transmitting surface thereof is orthogonal to the main polarization plane of the light source 2, a difference of transmission amounts between transmitted light that is transmitted through the site of FIG. 2(b) and transmitted through the polarizing filter 3 and transmitted light that is transmitted through the site of FIG. 2(c) and transmitted through the polarizing filter 3 is suppressed. As above, by blocking light of transmitted light transmitted through the image capturing target 5, which has the same polarization plane as the main polarization plane of the radiated light of the light source 2, by the polarizing filter 3, it is possible to obtain a captured image in which occurrence of brightness unevenness due to a thickness of a living body or the like is suppressed and reduced and biological information (in this case, brightness distribution obtained by absorption of infrared light in a vein) which is actually desired to be obtained is excellently reproduced. Thus, it is possible to use the obtained captured image for biometric authentication as it is without performing special image processing for the obtained captured image.

More specifically, in a case where an image is captured by radiating light from a backside of a finger and arranging the image sensor 4 on a pad side of the finger, the light is easily transmitted through a site corresponding to FIG. 2(c), that is, a knuckle part of the finger compared with a site corresponding to FIG. 2(b), that is, a pad part of the finger, and less likely to be affected by diffusion due to a living body. This is considered to be caused because a skin of a hand is thin at the knuckle part of the finger and the skin of the hand is thick at the pad part of the finger. Since light is less likely to be affected by diffusion at the knuckle part of the finger, transmitted light that has been transmitted through the knuckle part of the finger is transmitted while maintaining a polarization plane of radiated light, and contributes for brightly displaying the site corresponding to FIG. 2(c).

Accordingly, by blocking light of the transmitted light, which has been transmitted through the image capturing target 5 while maintaining the polarization plane, by the polarizing filter 3, it is possible to eliminate a main factor in brightly displaying the site corresponding to FIG. 2(c), thus making it possible to suppress occurrence of brightness unevenness between the site corresponding to FIG. 2(b) and the site corresponding to FIG. 2(c). Thereby, it is possible to obtain a captured image that is clear throughout the image capturing target 5 and to improve image capturing accuracy of the image capture device 1 according to the present embodiment.

Moreover, with the image capture device 1 according to the present embodiment, it is not necessary to arrange the light source 2 with close attention, so that it is possible to obtain a captured image that is clear throughout the image capturing target 5 while using a simple optical system. Thus, with the image capture device 1 according to the present embodiment, it is possible to improve image capturing accuracy while using a simple optical system.

In addition, since the image capturing accuracy of the image capture device 1 is improved, as to a biometric authentication device that includes the image capture device 1 according to the present embodiment, biometric authentication accuracy of the biometric authentication device that performs biometric authentication by using a captured image captured by the image capture device 1 is also improved. Such a biometric authentication device that includes the image capture device 1 according to the present embodiment is also included in the scope of the invention.

In the present embodiment, a case where the polarizing filter 3 is arranged so that the light-transmitting surface thereof is orthogonal to the main polarization plane of the light source 2 is exemplified. Such arrangement functions most effectively when radiated light from the light source 2 is vertically incident on the image capturing target 5 and transmitted therethrough and the transmitted light is detected by the image sensor 4 that is arranged on an optical axis direction of the light source 2.

Note that, although the light source 2, the image capturing target 5, the polarizing filter 3, and the image sensor 4 are arrayed in a direction of light output in the optical direction of the light source 2 in the present embodiment, a positional relation thereof is not limited thereto. By adjusting the positional relation, it is possible to prevent the radiated light from the light source 2 from being directly incident on the image sensor 4 without using the polarizing filter 3. However, the light radiated from the light source 2 is not completely linear light and is radiated with a certain constant expansion in a vertical direction and a horizontal direction.

For example, some representative infrared semiconductor lasers radiate light having an opening angle of about 20 degrees in the vertical direction and about 10 degrees in the horizontal direction. Thus, even when the image sensor 4 is arranged at a position which is shifted from an optical axis of the light source 2, light radiated in a direction other than the optical axis direction of the light source 2 is directly incident on the image sensor 4 in some cases. Therefore, even in such a case, it is necessary that the polarizing filter 3 is laid between the image capturing target 5 and the image sensor 4 so as to prevent the radiated light from the light source 2 from being directly incident on the image sensor 4. In this case, the light-transmitting surface of the polarizing filter 3 is only required to be arranged so that a light amount of non-transmitted light that reaches the image sensor 4 from the light source 2 becomes minimum by taking a main polarization plane of the non-transmitted light into consideration.

Moreover, even when light radiated from the light source 2 is obliquely incident on the image capturing target 5, the light-transmitting surface of the polarizing filter 3 is only required to be arranged so that a light amount that directly reaches the image sensor 4 becomes minimum by taking an inclination of the optical axis of the light source 2 with respect to the image sensor 4 into consideration in addition to the main polarization plane of the non-transmitted light that reaches the image sensor 4.

[Embodiment 2]

In general, when a semiconductor laser is used in a living space, a living body of a user, such as a retina, may be damaged. Therefore, the light source 2 that is used in the image capture device 1 according to the present embodiment is composed of an eye-safe laser in order to secure safety of a living body of a user, in particular, safety of an eye.

(Configuration of Light Source)

Figure 3:
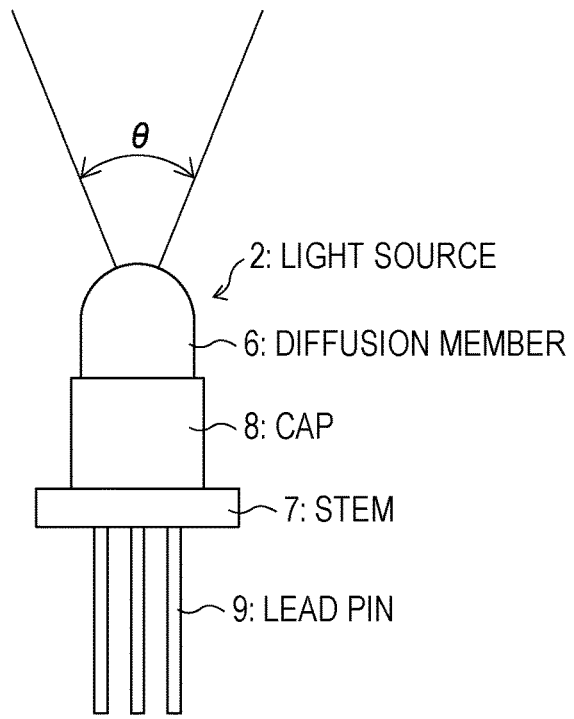
FIG. 3 is an external view illustrating the light source according to the embodiment of the invention.
Figure 5:
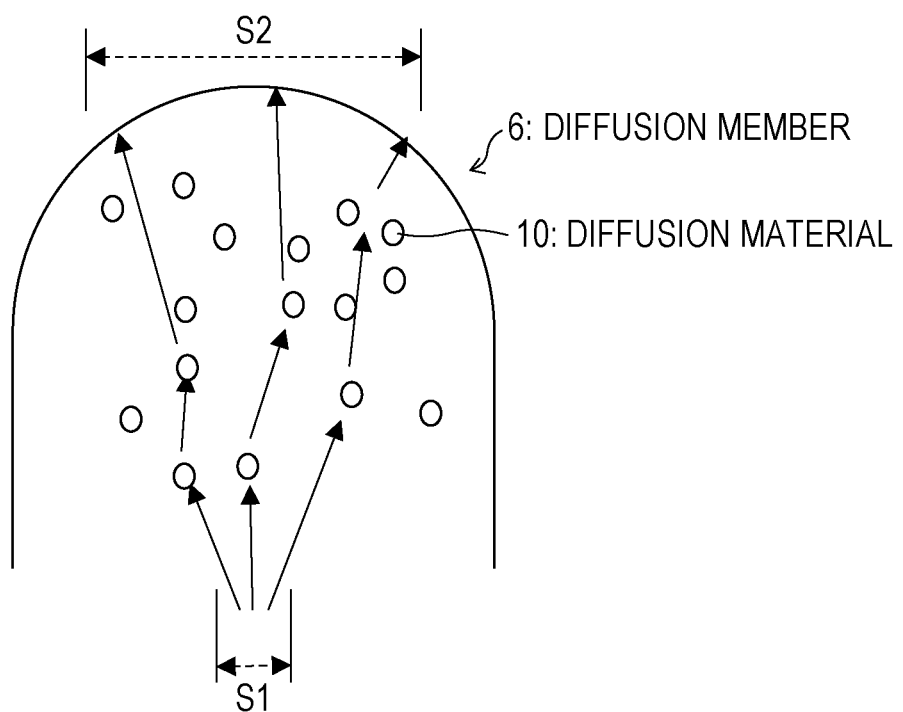
FIG. 5 is a view illustrating diffusion of light in a diffusion member of the light source according to the embodiment of the invention.
Figure 6:
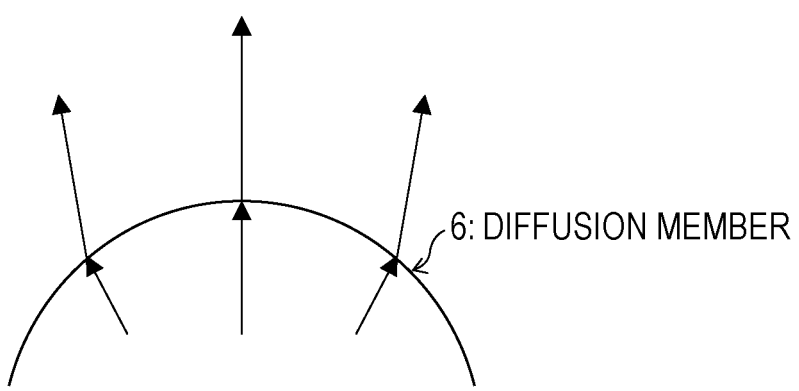
FIG. 6 is a view illustrating a shape of a surface of the diffusion member of the light source according to the embodiment of the invention.

The light source 2 according to the present embodiment will be described with reference to FIG. 3 to FIG. 6. FIG. 3 is an external view illustrating the light source 2, FIG. 4 illustrates a cross sectional view illustrating a semiconductor laser chip 12 of the light source 2, FIG. 5 illustrates diffusion of light in a diffusion member 6 of the light source 2, and FIG. 6 illustrates a shape of a surface of the diffusion member 6 of the light source 2.

As illustrated in FIG. 3, the light source 2 is a semiconductor laser of a CAN type package. Specifically, the light source 2 includes the semiconductor laser chip (not-illustrated), the diffusion member 6, a stem 7, a cap 8, and lead pins 9. The stem 7 is a part serving as a base and the cap 8 is fixed on one end surface thereof. The stem 7 has a plurality of through holes for arranging the lead pins 9 and each of the lead pins 9 is fixed to the stem 7 in a state of being inserted into a corresponding one of the through holes.

The cap 8 is an exterior member that stores various components including the semiconductor laser chip. The cap 8 includes, on an end on a side opposite to the stem 7, the diffusion member 6 that transmits light emitted from the semiconductor laser chip.

Figure 4:
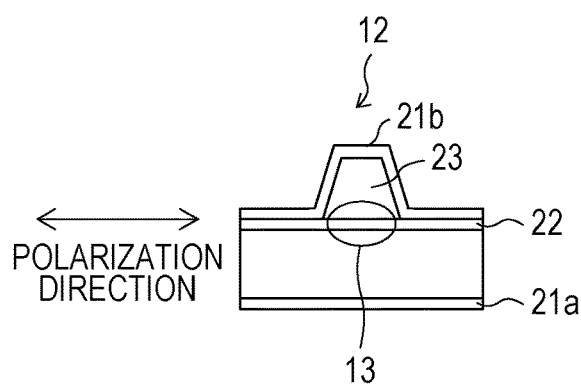
FIG. 4 is a cross sectional view illustrating a semiconductor laser chip of the light source according to the embodiment of the invention.

The semiconductor laser chip is, for example, a semiconductor laser chip 12 of a ridge stripe type, in which a light-emitting layer (active layer) 22 and a ridge stripe 23 are laid between an electrode 21*a* and an electrode 21*b* as illustrated in FIG. 4. As described above, the semiconductor laser chip 12 emits, from the cleaved end surfaces of the semiconductor laser chip 12, light having a specific polarization plane.

As illustrated in FIG. 5, the diffusion member 6 is formed of transparent resin, glass, or the like and an inside thereof is filled with a diffusion material 10 such as filler. The filler used as the diffusion material 10 is, for example, an inorganic material such as silica, alumina, titanium oxide, or zirconia, or a compound thereof.

Light radiated from the semiconductor laser chip is diffused by the diffusion material 10 in the diffusion member 6 and emitted to an outside. Thus, although a light source size of the light source 2 is S1, the light radiated from the semiconductor laser chip is diffused in the diffusion member 6, so that an apparent light source size of the light source 2 is spread up to a size of S2. The apparent light source size of the light source 2 is enlarged in this manner to thereby secure safety of a living body of a user.

Note that, as illustrated in FIG. 6, the shape of the surface of the diffusion member 6 is a lens shape. By appropriately changing the lens shape of the surface of the diffusion member 6, it is possible to control a radiation angle θ of light that is radiated from the semiconductor laser chip and diffused in the diffusion member 6.

As described by using FIG. 4 and FIG. 5, an eye-safe laser light is realized by causing laser light to pass through the diffusion member 6, but a method of realizing the eye-safe laser light is not limited thereto. For example, the eye-safe laser light may be realized by forming a reflection surface, which is configured by an inclined surface or a carved surface, with use of a diffusion member including the diffusion material 10 with a high concentration and radiating laser light thereto. In this case, as described above, by appropriately changing a shape of the reflection surface, it is possible to control the radiation angle θ of the light radiated from the semiconductor laser chip. Alternatively, a method obtained by appropriately combining the above-described method of causing laser light to pass through the diffusion member 6 and the method of reflecting the laser light by the diffusion member may be used.

(Polarization Ratio of Light Source)

A polarization ratio is a ratio of intensity of light having the main polarization plane of the light source 2 to intensity of light having a polarization plane other than the main polarization plane of the light source 2. The polarization ratio of the light source 2 according to the present embodiment is preferably not less than 3, more preferably not less than 9.

When the polarization ratio of the light source 2 is not less than 3, that is, light of radiated light from the light source 2, which is polarized to the main polarization plane, is not less than 75%, for example, in a configuration illustrated in FIG. 1, it is possible to block, by the polarizing filter 3, light of at least 75% of the non-transmitted light that has been radiated from the light source 2 and passed through the space or the periphery of the image capturing target 5 without being transmitted through the image capturing target 5.

This is because the non-transmitted light that has passed through the space or the periphery of the image capturing target 5 without being transmitted through the image capturing target 5 maintains the main polarization plane at a time of being radiated from the light source 2 as it is, and is therefore blocked by the polarizing filter 3 that is arranged so that the light-transmitting surface thereof is orthogonal to the main polarization plane of the radiated light of the light source 2. Accordingly, it is possible to prevent 75% of light, which has only passed through the space or the periphery of the image capturing target 5 without being transmitted through the image capturing target 5 and is polarized to the main polarization plane, from directly reaching the image sensor 4. It is thereby possible to suppress lack of biological information resulting from, for example, halation in a contour part of the image capturing target 5, thus making it possible to obtain a captured image suitable for performing biometric authentication.

Moreover, when the polarization ratio of the light source 2 is not less than 9, that is, light of radiated light from the light source 2, which is polarized to the main polarization plane, is not less than 90%, because of the same reason, it is possible to block, by the polarizing filter 3, light of at least 90% of the non-transmitted light that has passed through the space or the periphery of the image capturing target 5 without being transmitted through the image capturing target 5.

It is thereby possible to reliably suppress lack of biological information resulting from, for example, halation in the contour part of the image capturing target 5, so that contrast of biological information (for example, contrast between a vein part and a part other than the vein) becomes clear, and it is therefore possible to obtain a remarkably excellent captured image in which brightness distribution according to the biological information is clearly reproduced.

Note that, when the polarization ratio of the light source 2 is less than 2, that is, light of radiated light from the light source 2, which is polarized to the main polarization plane, is less than about 67%, an amount of light of the non-transmitted light which has been in the radiated light from the light source 2 and has passed through the space or the periphery of the image capturing target 5 without being transmitted through the image capturing target 5 and which is transmitted through the polarizing filter 3 without being blocked increases, so that a captured image becomes unclear.

The polarization ratio of the light source 2 is decided in accordance with a material and a concentration of the diffusion material 10 in the diffusion member 6, and a thickness of the diffusion member 6, and a finish condition of the surface thereof. Thus, the polarization ratio of the light source 2 is able to be controlled by appropriately adjusting the concentration of the material and the thickness of the diffusion member 6 in accordance with the material that is used as the diffusion material 10.

[Modified Example of Embodiment 2]

An eye-safe laser to be used as the light source 2 of the image capture device 1 is not limited to the semiconductor laser of the CAN type package, which is exemplified in Embodiment 2, and may be a semiconductor laser of a surface mount package (SMD package), for example.

Figure 7:
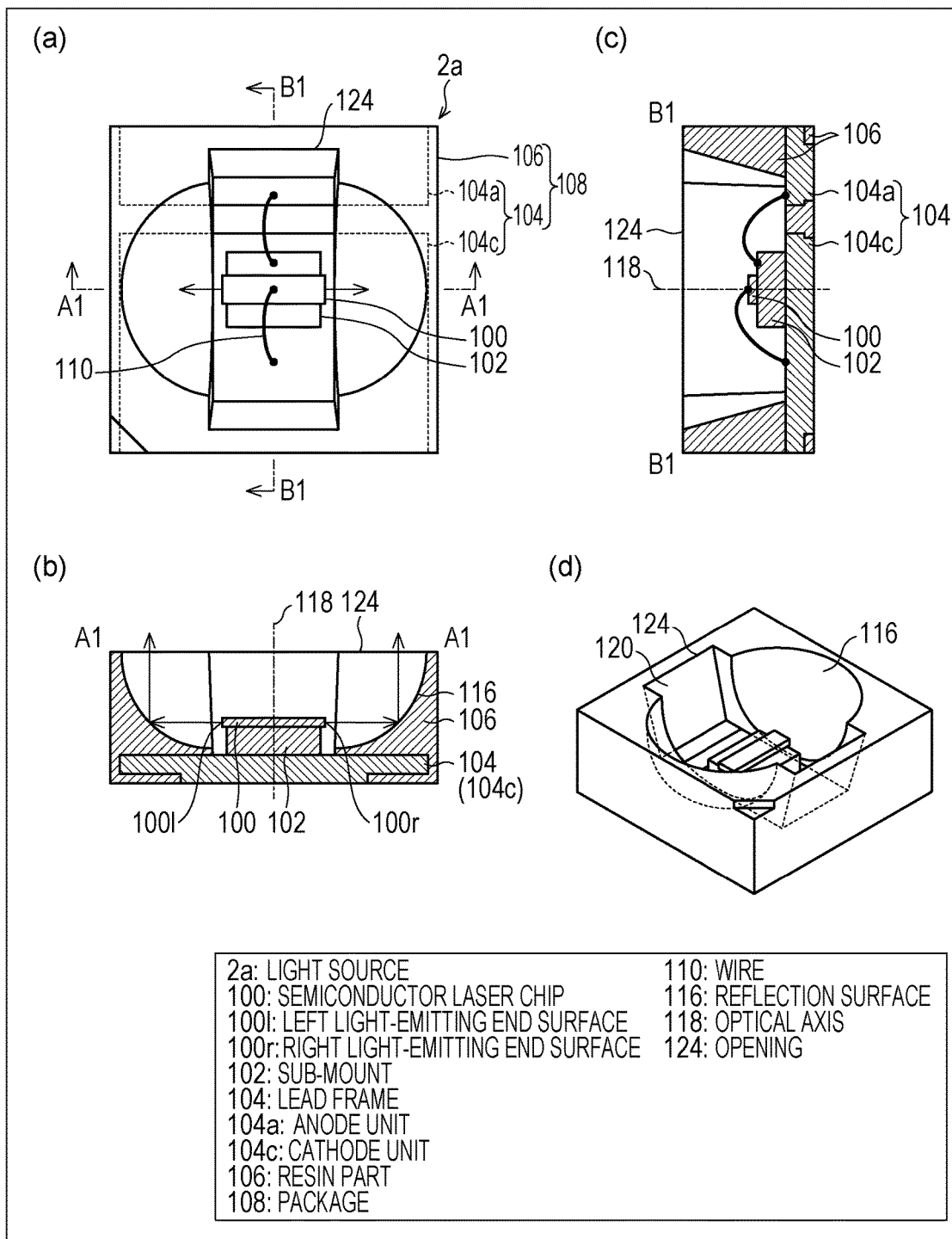
FIG. 7 is a view illustrating a schematic configuration of a periphery of a semiconductor laser chip of a light source according to an embodiment of the invention, in which (a) illustrates a top view obtained by seeing through a resin part, (b) is a cross sectional view taken along an arrow of A1-A1 of (a), (c) is a cross sectional view taken along an arrow of B1-B1 of (a), and (d) is a perspective view for illustrating a three-dimensional shape of the resin part.

Then, the semiconductor laser of the surface mount package (SMD package), which may be used as the light source according to the invention, will be described with reference to FIG. 7. FIG. 7 is a view illustrating a schematic configuration of a periphery of a semiconductor laser chip of a light source 2a according to the present embodiment, in which (a) illustrates a top view obtained by seeing through a resin part, (b) is a cross sectional view taken along an arrow of A1-A1 of (a), (c) is a cross sectional view taken along an arrow of B1-B1 of (a), and (d) is a perspective view for illustrating a three-dimensional shape of the resin part.

As illustrated in FIG. 7, the light source 2a includes a semiconductor laser chip 100 that radiates laser light from both of a left light-emitting end surface 100l arranged on a left side and a right light-emitting end surface 100r arranged on a right side, a sub-mount 102 on which the semiconductor laser chip 100 is mounted, a package (substrate) 108 that includes a metal-made lead frame (hereinafter, referred to as a lead frame for short) 104 and a resin part 106, and a wire 110.

The package 108 is a member in which a periphery of the lead frame 104 is partially covered (packaged) with the resin part 106. In the resin part 106, reflection surfaces 116 by which the laser light radiated by the semiconductor laser chip 100 is reflected are formed.

Examples of resin to be used for the resin part 106 include PCT resin and PPA resin which are generally used for a package of an LED light source. With use of such resin, it is possible to mold the reflection surfaces 116 by injection molding. However, the resin and the molding method are not limited thereto. As the resin, epoxy resin, silicone resin, and the like may be used in addition to the above-described resin, and transfer molding and a compression molding method may be used as the molding method. Moreover, resin including thermoplastic resin, thermosetting resin, UV-curing resin, or the like which are usually used for a light-emitting element of an LED may be used usually, and a molding method which is used for a light-emitting element of an LED may be used.

The lead frame 104 includes an anode unit 104a and a cathode unit 104c, and is electrically connected to each of a cathode of the semiconductor laser chip 100 and an anode of the semiconductor laser chip 100 via an electrode pattern (not illustrated) that is formed on the wire 110 and the sub-mount 102.

The semiconductor laser chip 100 oscillates with power supplied via the anode unit 104a and the cathode unit 104c of the lead frame 104, and symmetrically radiates laser light from the left light-emitting end surface 100l and the right light-emitting end surface 100r. The light radiated from the left light-emitting end surface 100l and the light radiated from the right light-emitting end surface 100r are respectively reflected by the left and right reflection surfaces 116 which are formed in the resin part 106 to thereby rise, and radiated to an outside of the package 108 via an opening 124. Although an optical axis 118 is set to be vertical to the lead frame 104 in the present embodiment, it is possible to incline the optical axis with respect to the lead frame 104 by changing shapes of the reflection surfaces 116.

(Realizing Eye-safe Laser Light, and Light Distribution Characteristics and Polarization Ratio)

A semiconductor laser chip that is generally used radiates not an ideal linear light beam but light having an opening angle of, for example, about 20 degrees in the vertical direction and about 10 degrees in the horizontal direction with respect to a resonator of the semiconductor laser chip at a time when the light is radiated from a light-emitting end surface. Therefore, although an apparent light source size of the light source 2a illustrated in FIG. 7 immediately after radiation of the semiconductor laser chip 100 is from several μm to more than 10 μm approximately, when being radiated from an end surface of the light source 2a, light is reflected by the reflection surfaces 116, and thus the apparent light source size is sufficiently enlarged compared with the original light source size.

In this manner, by enlarging the apparent light source size of the light source 2a, safety of a living body of a user is secured. Furthermore, by forming the reflection surfaces 116 with resin, an eye-safe property is enhanced compared with a case where a mirror surface is used as the reflection surfaces 116.

Figure 8:
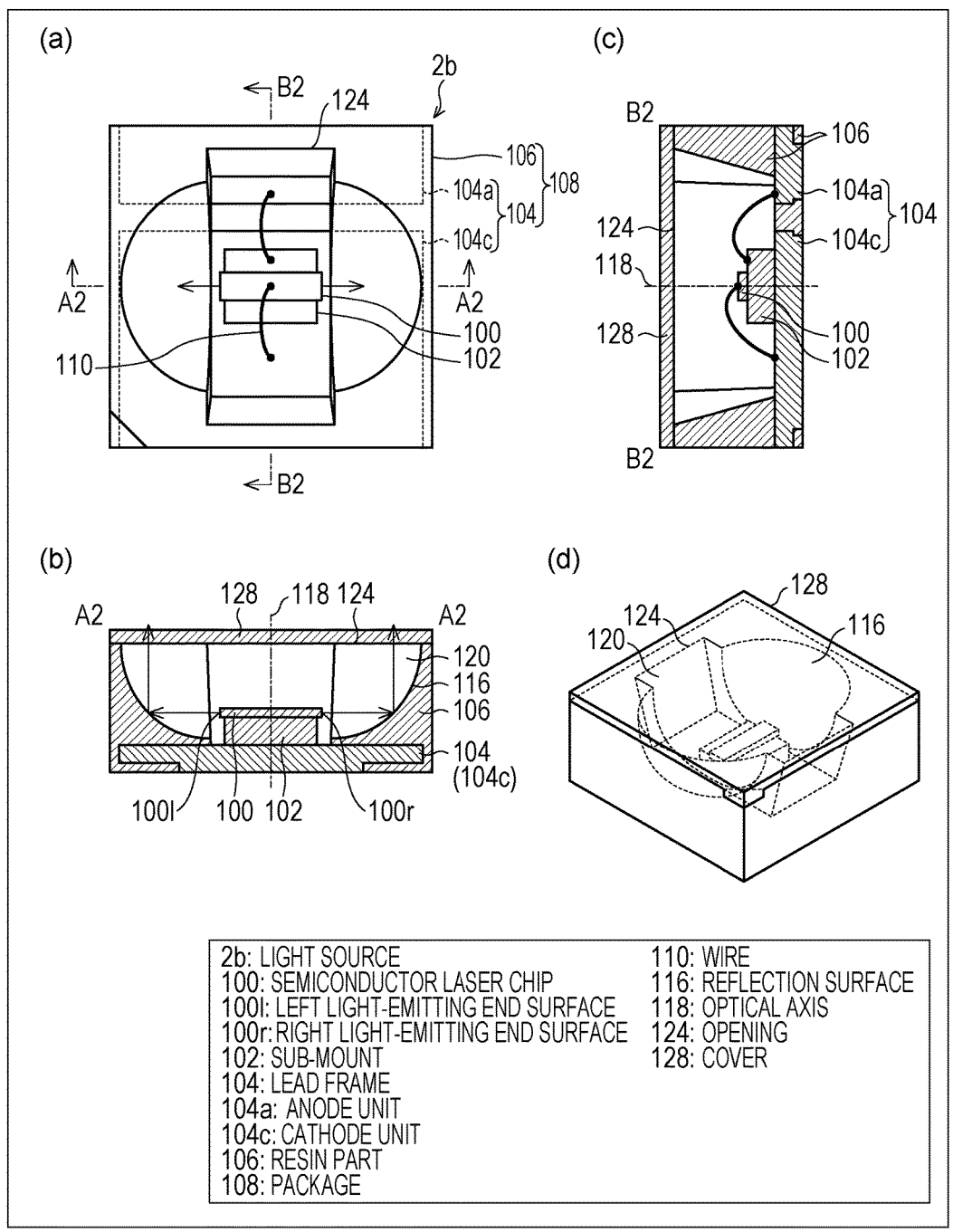
FIG. 8 is a view illustrating a schematic configuration of a periphery of a semiconductor laser chip of a light source provided with a cover according to the embodiment of the invention, in which (a) illustrates a top view obtained by seeing through a resin part, (b) is a cross sectional view taken along an arrow of A2-A2 of (a), (c) is a cross sectional view taken along an arrow of B2-B2 of (a), and (d) is a perspective view for illustrating a three-dimensional shape of the resin part.

A modified example of the light source 2a illustrated in FIG. 7 is illustrated in FIG. 8. FIG. 8 is a view illustrating a schematic configuration of a periphery of a semiconductor laser chip of a light source 2b provided with a cover 128, in which (a) illustrates a top view obtained by seeing through a resin part, (b) is a cross sectional view taken along an arrow of A2-A2 of (a), (c) is a cross sectional view taken along an arrow of B2-B2 of (a), and (d) is a perspective view for illustrating a three-dimensional shape of the resin part.

As illustrated in FIG. 8, the cover 128 that is optically transparent may be arranged outside the opening 124. By causing the cover 128 to contain a diffusion material such as filler and adjusting a thickness of the cover and a concentration of the diffusion material, it is possible to adjust light distribution characteristics and a polarization ratio of the light source 2b in accordance with a purpose. The filler used as the diffusion material is, for example, an inorganic material such as silica, alumina, titanium oxide, or zirconia, or a compound thereof.

Although a representative value of a polarization ratio of the light source 2a illustrated in FIG. 7 is, for example, about 60 to 100, in the light source 2b illustrated in FIG. 8, it is possible to adjust the polarization ratio between 2 to 100 by adjusting the thickness of the cover 128 and the concentration of the diffusion material contained in the cover.

[Embodiment 3]
(Hybrid of Transmission Type Image Capture Device and Reflection Type Image Capture Device)

Figure 9:
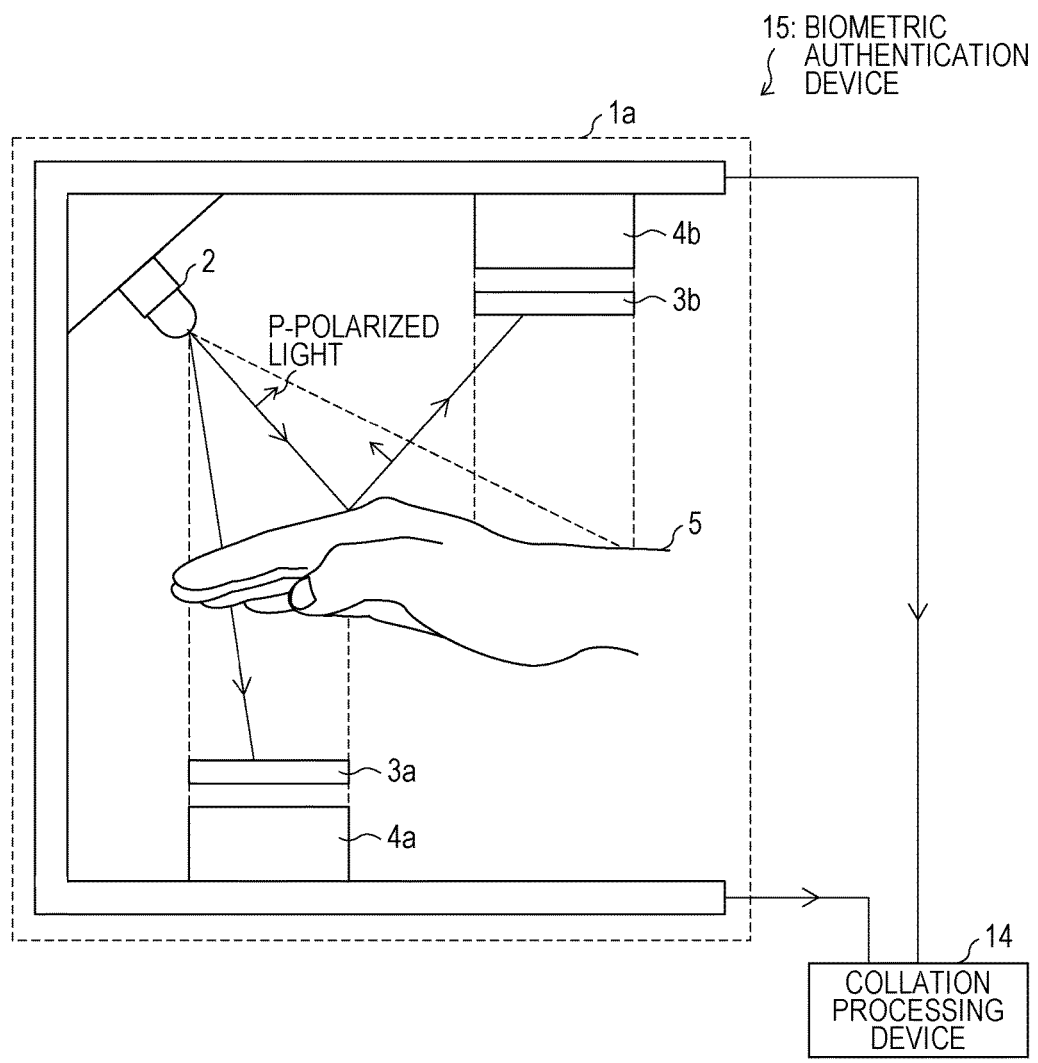
FIG. 9 is a schematic view illustrating a biometric authentication device according to an embodiment of the invention.

An embodiment of a biometric authentication device including the image capture device according to the invention is illustrated in FIG. 9. FIG. 9 is a schematic view of the biometric authentication device according to the present embodiment. Hereinafter, a case where a vein pattern of a hand of a user is acquired by capturing an image of the hand will be cited as an example to thereby describe the biometric authentication device according to the present embodiment.

As illustrated in FIG. 9, a biometric authentication device 15 includes an image capture device 1a and a collation processing device 14. The image capture device 1a includes the light source 2, a first polarizing filter 3a, and a first image sensor 4a. The light source 2 radiates polarized light of an infrared ray from a backside of a hand that is the image capturing target 5. Moreover, the first image sensor 4a is arranged on a side of a surface (in this case, a palm side of the hand) opposite to a light incident surface of the image capturing target 5, and the first polarizing filter 3a is arranged between the first image sensor 4a and the image capturing target 5.

The first polarizing filter 3a and the first image sensor 4a respectively correspond to the polarizing filter 3 and the image sensor 4 that are illustrated in FIG. 1. Accordingly, the first polarizing filter 3a is arranged so that a light-transmitting surface thereof is orthogonal to the main polarization plane of the light source 2, and blocks non-transmitted light that has been in light radiated from the light source 2 and has not been transmitted through the image capturing target 5 and transmitted light that has been in the radiated light and has been transmitted through the image capturing target 5 without diffusion inside the image capturing target 5, and transmits transmitted light which has been in the radiated light and has been diffused inside the image capturing target 5 and transmitted therethrough.

The first image sensor 4a receives the light transmitted through the first polarizing filter 3 and captures an image of the image capturing target 5 to thereby generate a captured image in which brightness distribution according to a vein pattern of a palm side of the hand (in particular, a pad side of a finger) that is the image capturing target 5 is reproduced.

The image capture device 1a further includes a second polarizing filter 3b and a second image sensor 4b. The second image sensor 4b is arranged on a side of the light incident surface (in this case, the backside of the hand) of the image capturing target 5, and the second polarizing filter 3b is arranged between the second image sensor 4b and the image capturing target 5. The second polarizing filter 3b is arranged so that a light-transmitting surface thereof is orthogonal to the main polarization plane of the light source 2.

When light is radiated from the light source 2 to the image capturing target 5, a part of the radiated light is mirror-reflected by a surface of the image capturing target 5, and reflected in a state where a polarization plane of incident light is maintained. On the other hand, a different part of the radiated light from the light source 2 is taken inside the image capturing target 5 and, while repeatedly being diffuse-reflected in the inside, in this process, a part of the light is absorbed by a vein and emitted from a skin surface in a state where no specific polarization plane is included.

Therefore, the second polarizing filter 3b blocks mirror-reflected light that has been in the light radiated from the light source 2 and has been mirror-reflected by the surface of the image capturing target 5 and transmits diffuse-reflected light which has been in the radiated light and diffuse-reflected inside the image capturing target 5.

The second image sensor 4b receives the light transmitted through the second polarizing filter 3b and captures an image of the image capturing target 5 to thereby generate a captured image in which brightness distribution according to a vein pattern of the backside of the hand that is the image capturing target 5 is reproduced.

In this manner, in the biometric authentication device 15, it is possible to obtain two captured images of a captured image of a pad side of a finger and a captured image of a backside of a hand. The collation processing device 14 collates vein information of the pad side of the finger and vein information of the backside of the hand, each of which is included in the corresponding captured image, with vein information that has been collected in advance, and thereby performs biometric authentication. The biometric authentication device 15 is able to obtain a plurality of pieces of biological information at once and perform biometric authentication by using the plurality of pieces of biological information, so that it is possible to improve accuracy of biometric authentication.

Here, the light source 2 may be arranged so that a main polarization plane of light that is obliquely radiated from the light source 2 to the image capturing target 5 becomes a P-polarization plane. It is thereby possible to suppress mirror-reflection by the surface of the image capturing target 5, and an amount of light that enters a living body increases. As a result, a captured image obtained by the second image sensor 4b becomes clearer, and image capturing accuracy of the image capture device 1a is improved.

Figure 10:
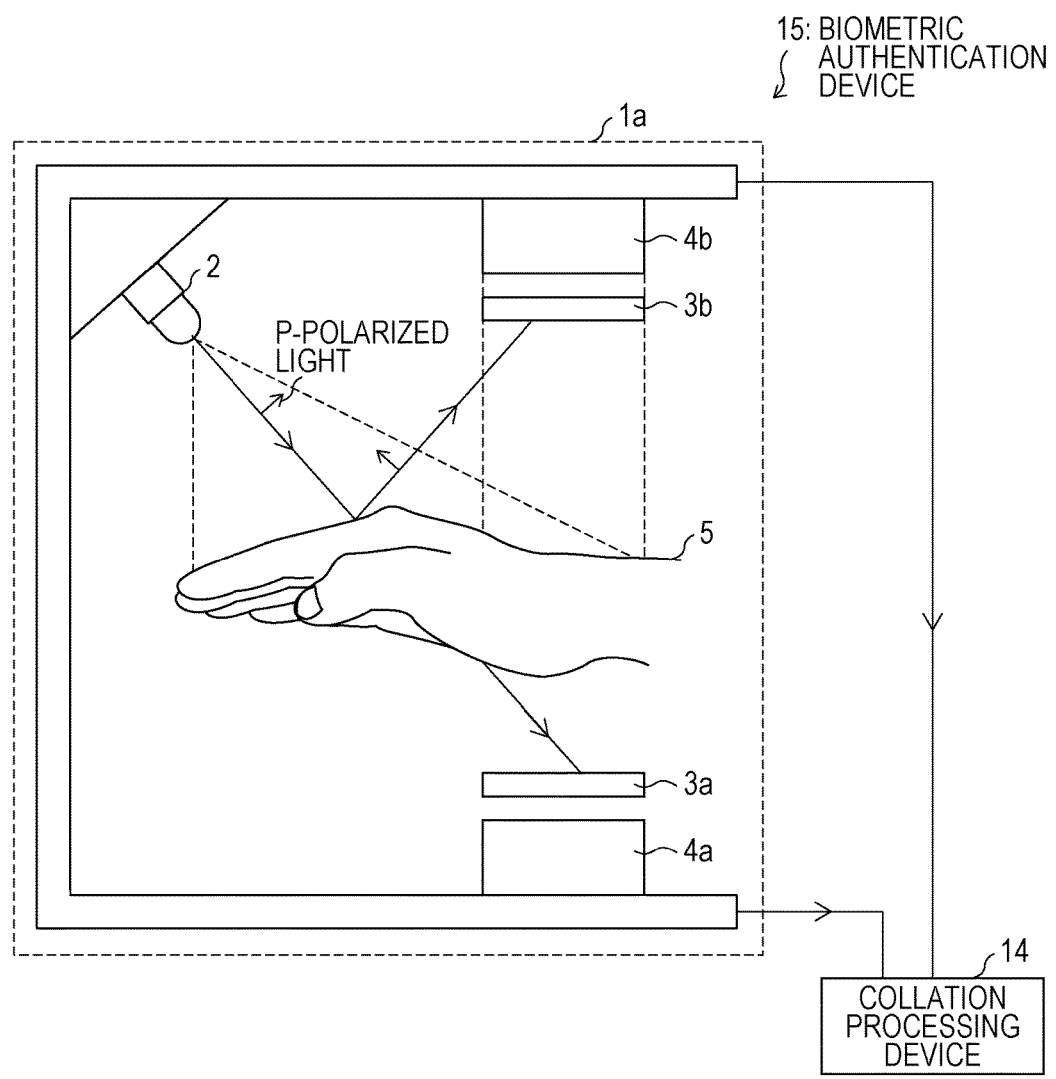
FIG. 10 is a schematic view illustrating a biometric authentication device according to the embodiment of the invention.

Note that, positions of the first polarizing filter 3a and the first image sensor 4a are not particularly limited as long as being positions which transmitted light transmitted through the image capturing target 5 reaches. For example, as illustrated in FIG. 10, the first polarizing filter 3a and the first image sensor 4a may be arranged on the optical axis of the light source 2. FIG. 10 is a schematic view of a biometric authentication device in a case where the first polarizing filter 3a and the first image sensor 4a are arranged on the optical axis of the light source 2.

The biometric authentication device 15 as above is generally considered to be used for financial settlement represented by an automatic teller machine (ATM), a key of a car or a house, security in a company or a multiple dwelling house, and the like, but is not limited to be used therefor, and practical use as a biometric authentication device in a place such as an international trade fair, a stadium, a theater, a concert hall, an amusement park, or a recreation park, in which a great number of people gather, is expected. Since it is necessary to perform processing for a large amount of security information in short time in such a place, the image capture device according to the invention, which is capable of obtaining clear biological information in a moment, is an image capture device suitable for a biometric authentication device in such a place.

[Conclusion]

An image capture device 1 according to an aspect 1 of the invention is the image capture device 1 that captures, as an image capturing target 5, an image of a site including biological information, and includes: a light source 2 that radiates polarized light of an infrared ray; a polarizing filter 3 that blocks non-transmitted light that has been in the polarized light radiated from the light source 2 and has not been transmitted through the image capturing target 5 and transmitted light that has been in the polarized light and has been transmitted through the image capturing target 5 without diffusion inside the image capturing target 5, and transmits transmitted light that has been in the polarized light and has been diffused inside the image capturing target 5 and transmitted therethrough; and an image sensor 4 that receives the light that has been transmitted through the polarizing filter 3 and captures an image of the image capturing target 5.

When non-transmitted light that has passed through a space or a periphery of the image capturing target 5 enters the image sensor 4 without passing through the polarizing filter 3, since intensity of the light of the non-transmitted light is higher than that of transmitted light that has been diffused inside the image capturing target 5 and transmitted therethrough, a captured image is saturated in a part that the non-transmitted light reaches. Moreover, the non-transmitted light causes halation, so that a ridge line of the image capturing target 5 becomes unclear. Then, according to the aforementioned configuration, since the non-transmitted light that has not been transmitted through the image capturing target 5 is blocked by the polarizing filter 3, it is possible to prevent the non-transmitted light from causing halation and the ridge line of the image capturing target 5 from being unclear.

Moreover, in a part at which a thickness of a living body is thin, compared with a part at which the thickness of the living body is thick, light is easily transmitted and an amount of transmitted light that is transmitted through the image capturing target 5 without diffusion inside the image capturing target 5 is large. There is a possibility that a difference of the amounts of the transmitted light causes brightness unevenness in a captured image and necessary biological information is not reproduced in the captured image. Then, according to the aforementioned configuration, since the transmitted light that has been transmitted through the image capturing target 5 without diffusion inside the image capturing target 5 is blocked by the polarizing filter 3, it is possible to suppress and reduce occurrence of brightness unevenness.

Thereby, it is possible to obtain a captured image that is clear throughout the image capturing target 5 and to improve image capturing accuracy of the image capture device 1 according to the present embodiment. Moreover, with the image capture device 1 according to the aspect of the invention, it is not necessary to arrange the light source 2 with close attention, so that it is possible to obtain a captured image that is clear throughout the image capturing target 5 while using a simple optical system. Thus, with the image capture device 1 according to the aspect of the invention, it is possible to improve image capturing accuracy while using the simple optical system.

In the image capture device 1 according to an aspect 2 of the invention, in the aspect 1, the polarizing filter 3 is arranged so that a light-transmitting surface thereof is orthogonal to a main polarization plane of the light source 2.

According to the aforementioned configuration, since polarization planes of the non-transmitted light which has been in the light radiated from the light source 2 and has not been transmitted through the image capturing target 5 and the transmitted light which has been in the radiated light and has been transmitted through the image capturing target 5 without diffusion inside the image capturing target 5 do not change, the light is not transmitted through the polarizing filter 3. On the other hand, since the transmitted light which has been in the light radiated from the light source 2 and has been diffused inside the image capturing target 5 and transmitted therethrough does not have a specific polarization plane, a part of the light is transmitted through the polarizing filter 3.

In this manner, it is possible to block, by the polarizing filter 3, the non-transmitted light that has not been transmitted through the image capturing target 5 and the transmitted light that has been transmitted through the image capturing target 5 without diffusion inside the image capturing target 5, so that it is possible to obtain a captured image in which brightness distribution of diffused transmitted light according to biological information is excellently reproduced.

In the image capture device 1 according to an aspect 3 of the invention, in the aspect 1 or 2, the light source 2 is a semiconductor laser.

According to the aforementioned configuration, the light radiated from the light source 2 has a specific wavelength and has a specific polarization plane. Thus, it is not necessary to use a filter such as a wavelength filter or a polarizing filter for the light source according to the aspect of the invention. Accordingly, it is possible to suppress loss of light, that is, reduction in intensity of light due to transmission through the filter. Thus, image capturing accuracy of the image capture device 1 according to the aspect of the invention is able to be improved. In addition, the filter is not required, so that the light source 2 is able to be made compact and also able to be mounted on mobile equipment. Furthermore, since the filter is not required to be provided, it is possible to suppress cost of the light source so as to be low.

Furthermore, with the semiconductor laser, it is possible to obtain a steep wavelength peak without passing through a wavelength filter on a light source side. Accordingly, by placing a cut filter having a window which is in conformity with the wavelength peak of the semiconductor laser in front of the image sensor 4, it is possible to effectively exclude disturbance light. That is, it is possible to receive light having a peculiar wavelength from the light source 2 by the image sensor 4 without being obstructed by disturbance light, thus making it possible to obtain information inside the image capturing target 5 by the light having the peculiar wavelength from the light source 2 without being obstructed by disturbance light. Thus, it is possible to further improve image capturing accuracy of the image capture device 1 only by placing the cut filter in front of the image sensor 4.

In the image capture device 1 according to an aspect 4 of the invention, in the aspect 3, the semiconductor laser is an eye-safe laser.

According to the aforementioned configuration, it is possible to secure safety of a living body of a user, specially, safety of an eye.

In the image capture device 1 according to an aspect 5 of the invention, in the aspect 4, a polarization ratio of the semiconductor laser is not less than 3, and preferably not less than 9.

According to the aforementioned configuration, it is possible to obtain a captured image suitable for biometric authentication.

A biometric authentication device 15 that includes the image capture device 1 according to any of the aspects 1 to 5 is also included in the scope of the invention.

Since image capturing accuracy of the image capture device 1 according to the aspect of the invention is improved, biometric authentication accuracy of the biometric authentication device 15 that includes the image capture device 1 is also improved.

Further, in the biometric authentication device 15 according to an aspect 6 of the invention, the light source 2 radiates polarized light of an infrared ray to a finger serving as the image capturing target 5 from a backside of the finger, the image sensor 4 is arranged on a pad side of the finger, the polarizing filter 3 is arranged between the finger and the image sensor 4, and biometric authentication is performed by using a captured image of the pad side of the finger, which is captured by the image sensor 4.

According to the aforementioned configuration, it is possible to perform biometric authentication by using a clear captured image that is obtained throughout the pad side of the finger.

In the biometric authentication device 15 according to an aspect 7 of the invention, in the aspect 6, the light source 2 is arranged so that the main polarization plane becomes a P-polarization plane.

According to the aforementioned configuration, when a main polarization plane of light that is obliquely incident on the image capturing target 5 is set to be a P-polarization plane, it is possible to suppress mirror-reflection by a surface of the image capturing target 5, and an amount of light enters a living body increases. As a result, a captured image obtained by the image capture device becomes clearer, image capturing accuracy of the image capture device 1 is able to be improved, and biometric authentication accuracy of the biometric authentication device 15 is also improved.

In the biometric authentication device 15 according to an aspect 8 of the invention, in the aspect 6 or 7, the image capture device 1 further includes a second image sensor 4b that is arranged on the backside of the finger, and a second polarizing filter 3b that is arranged between the finger and the second image sensor 4b and that blocks light reflected from a surface of the finger and transmits light reflected inside the finger, and biometric authentication is performed by using the captured image of the pad side of the finger, which is captured by the image sensor 4, and a captured image of the backside of the finger or a backside of a hand, which is captured by the second image sensor 4b.

According to the aforementioned configuration, it is possible to obtain the captured image of the backside of the hand by the second image sensor 4b. Thereby, vein information of the pad side of the finger and vein information of the backside of the hand, each of which is included in the corresponding one of the captured image of the pad side of the finger and the captured image of the backside of the hand, are able to be obtained. By the biometric authentication device 15 according to the aspect of the invention, a plurality of pieces of biological information are able to be obtained at once in this manner, and it is possible to perform biometric authentication by using the plurality of pieces of biological information, so that it is possible to improve accuracy of biometric authentication.

REFERENCE SIGNS LIST 1 image capture device
2, 2a, 2b light source
3 polarizing filter
3a first polarizing filter
3b second polarizing filter
4 image sensor
4a first image sensor
4b second image sensor
5 image capturing target
15 biometric authentication device

The invention claimed is:

1. A biometric authentication device comprising:
an image capture device that captures, as an image capturing target, an image of a site including biological information, the image capture device comprising:
　a light source that radiates polarized light of an infrared ray, an apparent light source size of which being enlarged by light radiated from a semiconductor laser chip;
　a polarizing filter that blocks non-transmitted light that has been in the polarized light radiated from the light source and has not been transmitted through the image capturing target and transmitted light that has been in the polarized light and has been transmitted through the image capturing target without diffusion inside the image capturing target, and transmits transmitted light that has been in the polarized light and has been diffused inside the image capturing target and transmitted therethrough; and
　an image sensor that receives the light that has been transmitted through the polarizing filter and captures an image of the image capturing target,
wherein the light source radiates polarized light of an infrared ray to a finger serving as the image capturing target from a backside of the finger,
the image sensor is arranged on a pad side of the finger,
the polarizing filter is arranged between the finger and the image sensor, and
biometric authentication is performed by using a captured image of the pad side of the finger, which is captured by the image sensor.

2. The biometric authentication device according to claim 1, wherein
the image capture device further includes
　a second image sensor that is arranged on the backside of the finger, and
　a second polarizing filter that is arranged between the finger and the second image sensor and that blocks light reflected from a surface of the finger and transmits light reflected inside the finger, and
　biometric authentication is performed by using the captured image of the pad side of the finger, which is captured by the image sensor, and a captured image of the backside of the finger, which is captured by the second image sensor.

* * * * *